(12) United States Patent
DeLuca, Jr.

(10) Patent No.: US 6,485,556 B1
(45) Date of Patent: Nov. 26, 2002

(54) INTERFERENCE PIGMENTS

(75) Inventor: Carmine V. DeLuca, Jr., Peekskill, NY (US)

(73) Assignee: Engelhard Corporation, NJ (US)

( * ) Notice: Subject to any disclaimer, the term of this patent is extended or adjusted under 35 U.S.C. 154(b) by 0 days.

(21) Appl. No.: 09/974,145

(22) Filed: Oct. 10, 2001

(51) Int. Cl.$^7$ ................................................ C04B 14/20
(52) U.S. Cl. .................... 106/415; 106/417; 106/418; 106/439; 106/441; 106/453; 106/456
(58) Field of Search ............................. 106/415, 417, 106/418, 439, 441, 453, 456

(56) References Cited

U.S. PATENT DOCUMENTS

| | | | | |
|---|---|---|---|---|
| 3,087,828 A | * | 4/1963 | Linton | 106/417 |
| 3,087,829 A | * | 4/1963 | Linton | 106/417 |
| 3,926,659 A | * | 12/1975 | Bernhard et al. | 106/417 |
| 4,146,403 A | * | 3/1979 | Armanini et al. | 106/418 |
| 4,192,691 A | | 3/1980 | Armanini | |
| 4,482,389 A | * | 11/1984 | Franz et al. | 106/417 |
| 4,867,793 A | * | 9/1989 | Franz et al. | 106/415 |
| 5,302,199 A | * | 4/1994 | Prengel et al. | 106/415 |
| 5,364,467 A | * | 11/1994 | Schmid et al. | 106/403 |
| 5,607,504 A | * | 3/1997 | Schmid et al. | 106/403 |
| 5,611,851 A | * | 3/1997 | DeLuca et al. | 106/415 |
| 6,361,593 B2 | * | 3/2002 | DeLuca et al. | 106/415 |

* cited by examiner

Primary Examiner—Mark L. Bell
Assistant Examiner—Shalie Manlove
(74) Attorney, Agent, or Firm—Dickstein, Shapiro, Morin & Oshinsky, LLP

(57) ABSTRACT

Pearlescent pigment having a chromium coating thereon and an iron oxide coating on the chromium coating are intensely colored, almost phosphorescently colored, and are highly reflective.

20 Claims, No Drawings

INTERFERENCE PIGMENTS

BACKGROUND OF THE INVENTION

Nacreous pigments, also known as pearlescent or effect pigments, exhibit pearl-like and/or iridescent effects upon the transmission and reflection of light therethrough. As is well known in the art, the characteristics of such pigments depends upon optical interference phenomena as more fully described, for example, in "The Properties of Nacreous Pigments", Greenstein and Miller, Technical Papers, Vol. XIII, Annual Technical Conference, Society of Plastic Engineers, May 1967.

Nacreous pigments are conventionally formulated for use in suspensions of light transmitting resinous media which can be applied by dipping or spraying operations to form plastic coatings or by extruding, molding, casting or like techniques to provide solid plastic articles incorporating such pigments. Nacreous pigments so utilized should have indexes of refraction which differ from the suspending media because the pearly or nacreous effect displayed by such pigments depends upon the difference between the index of refraction of the oriented, plate-like pigment particles and the index of refraction of the medium in which they are dispersed.

Mica by itself is not a satisfactory nacreous pigment inasmuch as its average index of refraction is about 1.58 which is too close to the index of conventional transparent resinous media of about 1.5–1.59. Excellent nacreous pigments may, however, be provided by the deposition of titanium dioxide or iron oxide coatings on mica flakes.

Linton U.S. Pat. Nos. 3,087,828 and 3,087,829 describe the preparation of titanium dioxide and other metal oxide coated mica nacreous pigments, which optionally can be topped with a layer of another material such as, inter alia, iron and chromium.

Armanini, et al. U.S. Pat. No. 4,146,403 describes iron oxide-coated mica nacreous pigments which are improved by interposing a thin layer of titanium dioxide or aluminum oxide between the iron oxide and the mica. Dark colors and a very good adhesion of the iron oxide layer is obtained.

Pearlescent or nacreous pigments are frequently evaluated by examining or measuring reflectance by means of conventional drawdowns on a hiding power chart. For instance, drawdowns are prepared from a suspension containing 3% pigment in a nitrocellulose lacquer as described, inter alia, in the aforementioned Armanini, et al. patent.

The pearlescent pigments are conventionally used to color various materials. They can be incorporated, for instance, in plastics or coated on a substrate using conventional techniques. In such applications, the pearlescent plastics exhibit a constant pearlescent effect. It has now been surprisingly discovered that certain pearlescent pigments exhibit a unique effect when coated on a color card, a metallic substrate, incorporated into a plastic chip, etc. More particularly, these pigments exhibit are intensely colored, almost phosphorescently colored, and are highly reflective.

SUMMARY OF THE INTENTION

This invention is related to new articles exhibiting an intense color and high reflectivity and their preparation. More particularly, the invention relates to a platelet pearlescent pigment having a chromium coating on titanium dioxide platelets and an iron oxide coating on the chromium coating.

DETAILED DESCRIPTION OF THE INVENTION

The pearlescent pigments used in the present invention are iron oxide-coated chromium-coated titanium dioxide platelet nacreous pigments. These titanium dioxide platelet nacreous pigments are derived from titanium dioxide-coated mica substrate from which the substrate has been removed and are, in the general sense, known. Any known procedures can be used to prepare such pigments. The formulation of coating compositions containing such pigments and the coating of substrates is likewise known.

Titanium dioxide platelets suitable for use in this invention are described, for instance in U.S. Pat. Nos. 4,192,691 and 5,611,851, which are incorporated herein for their teaching of titanium platelets and methods for their manufacture. Such platelets are commonly referred to as "platy $TiO_2$" or "self supporting $TiO_2$" and are substantially substrate free, generally containing less than about 20% of substrate based on the total weight of the product. U.S. Pat. No. 4,192,691 employs an aqueous solution of hydrofluoric acid and a mineral acid such as sulfuric acid to dissolve the mica from the pigment. It also discloses and illustrates the use of this dissolving agent to remove the mica from a titanium dioxide-coated mica having a surface layer of either iron or chromium oxide. U.S. Pat. No. 5,611,851 employs a combination of a mineral acid and phosphoric acid followed by an extractive dissolution using an alkali. Although the procedure of U.S. Pat. No. 5,611,851 is preferred, other procedures can be employed to obtain the titanium dioxide platelets used in the present invention.

The $TiO_2$ platelet types useful in this invention can be prepared via the web method, using fluid bed techniques, hydrolyzing organic titanates or homogeneous precipitation employing $NaOH/TiCl_4$. In addition, platelet $TiO_2$ suitable for this invention can be prepared by removing gypsum from $TiO_2$ coated gypsum or by burning off graphite from $TiO_2$ coated graphite. Dissolving glass from a $TiO_2$ coated glass base also provides a substrate useful in this invention. Although there are several avenues for preparing the Ti which then can be coated further, the $TiO_2$ substrate of U.S. Pat. No. 5,611,851 still preferred in order to obtain maximum reflectivity and color purity.

The platelets of titanium dioxide are generally about 1–75 $\mu$m in length, preferably about 2–35 $\mu$m, and have an interference thickness of about 5–600 nm, preferably about 20–400 nm. By substantially substrate-free is meant that the platelet material can incorporate up to about 20% of the mica substrate and usually incorporate at least 1% mica. The $TiO_2$ is preferably in the rutile crystalline form but can also be in the anatase form.

Providing a titanium dioxide-coated mica with a surface layer of either iron or chromium oxide is known. In broad terms, the material to be coated is brought into contact with a salt of the metal, usually an aqueous solution thereof, under appropriate conditions, e.g. pH, so as to deposit a layer of the metal, followed by calcination. The present invention utilizes such known procedures but differs therefrom in that titanium dioxide platelet is used as the material to be coated, both chromium and iron are deposited thereon and the chromium is deposited first. The chromium layer is preferably partly calcined before the iron is deposited but can be fully calcined if desired. To achieve partial calcination, a lower calcination temperature of about 350–500° C., preferably about 425–475° C., is employed for about 0.1–5 hours, preferably 0.25–0.75 hour. In general, the chromium will constitute about 2–8%, preferably about 4–5%, of the final calcined product and the iron will constitute about 4–10%, preferably about 6–7%, of the final calcined product.

After the iron is deposited and final calcining, the reflectivity is increased and the interaction between Ti, Cr and Fe returns an intense, almost phosphorescent color. Colors between gold and green, within the interference spectrum, can be prepared. In each case, reflectivity increases with intense color formation. This is the first time such an effect has been recorded or reported, using a substrate-free interference type $TiO_2$ substrate. Compared to prior art, this process has several advantages. It employs standard, pearlescent coating technology without resorting to solvent based reactions or chemical vapor deposition/reduction techniques, it takes full advantage of the high refractive index of $TiO_2$ (2.6–2.9) without mica presence, it does not require costly or impractical equipment, and it produces a full range of colors which can be used in cosmetic/automotive/industrial markets.

The following examples are set forth in order to further illustrate the invention without being intended to limit it. Throughout the specification and claims, all parts and percentages are by weight and all temperatures and degrees are centigrade unless otherwise indicated.

EXAMPLES 1–6

One hundred thirty grams of a red interference $TiO_2$ coated mica was treated with an acid dissolution step followed by alkali leaching in a second step, as described in U.S. Pat. No. 5,611,851, to prepare approximately 80 grams of a red interference $TiO_2$ platelets which were slurried in 1 liter of deionized water. The slurry was stirred at 250–300 rpm and the pH was adjusted to 6.5–7.0 using HCl and/or NaOH as necessary. At 25° C. 200 g of 10% $CrCl_3.6H_2O$ was added at the rate of 2.0 ml/min while maintaining the pH constant at 6.5–7.0 by appropriate additions of NaOH. Following completion of the chromium addition, the solid was filtered, and the resulting presscake was washed and calcined for ½ hr. at 450° C. After the partial calcination, the crystals were re-slurried in 1 liter of deionized water and heated to 74° C. At room temperature, the pH was adjusted to 3.5. Then, 30 ml of 39% aqueous $FeCl_3$ was added at a rate of 0.5 ml/min, maintaining the pH constant at 3.5 to a purple colored product. The slurry was filtered, and the resulting presscake was washed and calcined at 850° C. for ½ hr. A deep and intense violet colored product was obtained, having a higher reflectivity compared to a platy $TiO_2$ exhibiting an inference violet color.

The forgoing procedure was repeated substituting different titanium dioxide platelets prepared by treating 120–130 grams of titanium dioxide coated mica. The results are st forth in the following table.

| Example | $TiO_2$ Initial Interference Color | Final Interference Color |
|---|---|---|
| 2 | green | green/gold |
| 3 | gold | orange |
| 4 | orange | red |
| 5 | violet | blue |
| 6 | blue | green |

In each case, the final reflection/absorption color was identical, very intense and exhibiting an increase in quality by reflection relative to platelet titanium dioxide of the same color.

EXAMPLE 7

The procedure of Example 1 was repeated omitting the chromium addition. A violet reflecting product was obtained but it had less color intensity than the product of Example 1.

EXAMPLE 8

The procedure of Example 1 was repeated substituting tin chloride for the chromium chloride. A violet reflecting product was obtained but it had less color intensity and reflectivity than the product of Example 1.

EXAMPLE 9

A colorant product prepared according to example 2 is incorporated into polypropylene step chips at 1% concentration. The step chips are appropriately named since they have graduating thickness at each step across the face of the chip. The graduating steps allow one to examine the different effect of the colorant based on polymer thickness.

EXAMPLE 10

A colorant product prepared according to example 2 is incorporated into a nail enamel. 10 g of the colorant is mixed with 82 g of suspending lacquer SLF-2, 4 g lacquer 127 P and 4 g ethyl acetate. The suspending lacquer SLF-2 is a generic nail enamel consisting of butyl acetate, toluene, nitrocellulose, tosylamide/formaldehyde resin, isopropyl alcohol, dibutyl phthalate, ethyl acetate, camphor, n-butyl alcohol and silica.

EXAMPLE 11

A 10% by weight colorant product from example 2 is sprayed in a polyester TGIC powder coating from Tiger Drylac using a PGI corona Gun #110347. The colorant is mixed in a clear polyester system and sprayed over a RAL 9005 black pigmented polyester powder. The colorant is highly attracted to the ground metal panel due to its electrical properties. Additionally, due to its high affinity to orient closely to the surface it produces a finish that is high in distinctness of image (DOI). It does not require an additional clear coat to reduce protrusion often caused by traditional pearlescent and metal flake pigments.

EXAMPLE 12

A 10% dispersion of the colorant product prepared according to example 2 is mixed into a clear acrylic urethane basecoat clearcoat paint system DBX-689 (PPG) along with various PPG tints to achieve desired color. The tint pastes consist of organic or inorganic colorants dispersed at various concentrations in a solventborne system suitable with the DMD Deltron Automotive Refinish paint line from PPG. The complete formulation is sprayed using a conventional siphon feed spraygun onto 4×12" curved automotive type panels supplied by Graphic Metals. The panel is clear coated with PPG 2001 high solids polyurethane clear coat and air dried.

Products of this invention have an unlimited use in all types of automotive and industrial paint applications, especially in the organic color coating and inks field where deep color intensity is required. For example, these pigments can be used in mass tone or as styling agents to spray paint all types of automotive and non-automotive vehicles. Similarly, they can be used on all clay/formica/wood/glass/metal/enamel/ceramic and non-porous or porous surfaces. They can be incorporated into plastic articles geared for the toy industry or the home. These pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies.

The above-mentioned compositions in which the compositions of this invention are useful are well known to those of ordinary skill in the art. Examples include printing inks, nail enamels, lacquers, thermoplastic and thermosetting materials, natural resins and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wiley and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282–591; with regard to paints: C. H. Hare, Protective Coatings, Technology Publishing Co., Pittsburgh (1994), particularly pages 63–288. The foregoing references are hereby incorporated by reference herein for their teachings of ink, paint and plastic compositions, formulations and vehicles in which the compositions of this invention may be used including amounts of colorants. For example, the pigment may be used at a level of 10 to 15% in an offset lithographic ink, with the remainder being a vehicle containing gelled and ungelled hydrocarbon resins, alkyd resins, wax compounds and aliphatic solvent. The pigment may also be used, for example, at a level of 1 to 10% in an automotive paint formulation along with other pigments which may include titanium dioxide, acrylic lattices, coalescing agents, water or solvents. The pigment may also be used, for example, at a level of 20 to 30% in a plastic color concentrate in polyethylene.

In the cosmetic field, these pigments can be used in the eye area and in all external and rinse-off applications. Thus, they can be used in hair sprays, face powder, leg-makeup, insect repellent lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, powder, stick, pressed or cream), eye liner, cologne stick, cologne, cologne emollient, bubble-bath, body lotion (moisturizing, cleansing, analgesic, astringent), after shave lotion, after bath milk and sunscreen lotion.

Various changes and modifications can be made in the process and products of this invention without departing from the spirit and scope of the invention. The various embodiments which were disclosed herein (including the field of use disclosure) were intended to further illustrate the invention but not to limit it.

What is claimed is:

1. A titanium dioxide nacreous pigment comprising platelets of titanium dioxide of about 1–75 $\mu$m in length and an interference thickness of about 5–600 nm and having a chromium coating thereon and an iron oxide coating on the chromium coating.

2. The pigment of claim 1, wherein the platelets are substantially substrate-free and have a length of about 2–35 $\mu$m and a thickness of about 20–400 nm, and contain at least 1% mica.

3. The pigment of claim 2, wherein the titanium dioxide is in the rutile crystalline form.

4. The pigment of claim 3, wherein the chromium is about 2–8% and the iron is 4–10% of the pigment.

5. The pigment of claim 4, wherein the chromium is about 4–5% and the iron is 6–7% of the pigment.

6. The pigment of claim 1, wherein the titanium dioxide is in the rutile crystalline form.

7. The pigment of claim 1, wherein the chromium is about 2–8% and the iron is 4–10% of the pigment.

8. The pigment of claim 7, wherein the chromium is about 4–5% and the iron is 6–7% of the pigment.

9. The pigment of claim 1, wherein the titanium dioxide is in the anatase crystalline form.

10. In a paint or ink composition including a pigment, the improvement which comprises said pigment being a pigment of claim 1.

11. In a plastic composition including a pigment, the improvement which comprises said pigment being a pigment of claim 1.

12. In a cosmetic composition including a pigment, the improvement which comprises said pigment being a pigment of claim 1.

13. A method of preparing the pigment of claim 1 which comprises providing a titanium dioxide nacreous pigment comprising platelets of titanium dioxide of about 1–75 $\mu$m in length and an interference thickness of about 5–600 nm depositing a hydrous chromium layer on the pigment, at least partly calcining the chromium coated pigment, depositing a hydrous iron layer on the chromium layer, and calcining the iron-coated, chromium-coated pigment.

14. The method of claim 13, wherein the chromium is deposited by slurrying the pigment in an aqueous chromium salt solution under deposition conditions.

15. The method of claim 14, wherein the at least partly calcining the chromium coated pigment comprises heating to a temperature of about 350–500° C. for about 0.1–5 hours.

16. The method of claim 15, wherein the iron is deposited by slurrying the chromium-coated pigment in an aqueous iron salt solution under deposition conditions.

17. The method of claim 16, wherein the chromium and iron are deposited so as to realize a chromium content of about 2–8% and an iron content of about 4–10% of the pigment.

18. The method of claim 17, wherein the chromium and iron are deposited so as to realize a chromium content of about 4–5% and an iron content of about 6–7% of the pigment.

19. The method of claim 13, wherein the at least partly calcining the chromium coated pigment comprises heating to a temperature of about 425–475° C. about 0.25–0.75 hours.

20. The method of claim 13, wherein the titanium dioxide nacreous pigment provided is substantially substrate-free.

* * * * *